United States Patent
Yamanishi et al.

(10) Patent No.: US 6,860,978 B2
(45) Date of Patent: Mar. 1, 2005

(54) BIOSENSOR AND METHOD OF PRODUCING THE SAME

(75) Inventors: Eriko Yamanishi, Ehime (JP); Shoji Miyazaki, Ehime (JP); Noriyoshi Terashima, Ehime (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 441 days.

(21) Appl. No.: 09/959,816
(22) PCT Filed: Mar. 8, 2001
(86) PCT No.: PCT/JP01/01812
§ 371 (c)(1),
(2), (4) Date: Dec. 18, 2001
(87) PCT Pub. No.: WO01/67081
PCT Pub. Date: Sep. 13, 2001

(65) Prior Publication Data
US 2002/0179441 A1 Dec. 5, 2002

(30) Foreign Application Priority Data
Mar. 8, 2000 (JP) ........................................ 2000-062855

(51) Int. Cl.[7] ............................................. G01N 27/327
(52) U.S. Cl. .................................................. 204/403.14
(58) Field of Search ....................... 204/403.01, 403.04, 204/403.09, 403.1, 403.11, 403.14, 416

(56) References Cited

U.S. PATENT DOCUMENTS

| 5,512,159 A | 4/1996 | Yoshioka et al. ...... 204/403.08 |
| 5,656,142 A | * 8/1997 | Park et al. ............... 204/403.1 |

FOREIGN PATENT DOCUMENTS

| EP | 0851224 A1 | 7/1998 | ......... G01N/27/327 |
| JP | 9-5288 | 1/1997 | ......... G01N/27/327 |
| JP | 11-101772 | 4/1999 | ......... G01N/27/327 |

* cited by examiner

*Primary Examiner*—Alex Noguerola
(74) *Attorney, Agent, or Firm*—Wenderoth, Lind & Ponack, L.L.P.

(57) ABSTRACT

A biosensor includes a pair of conductive lead parts formed on an insulating substrate, a working electrode and a counter electrode formed at the ends of the conductive lead parts, respectively, and a reaction layer formed so as to bridge the electrodes and react with a measurement target substance in a specimen liquid. The biosensor measures the content of the measurement target substance from an electric current value based on the reaction between the measurement target substance and the reaction layer, which current value is obtained through the pair of conductive lead parts. The reaction layer is not provided above at least one of the conductive lead parts so that the reaction layer and the conductive lead parts do not contact directly even when pin holes or cracks are generated in the electrodes.

4 Claims, 4 Drawing Sheets

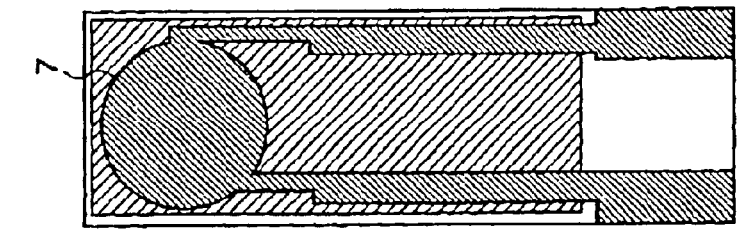
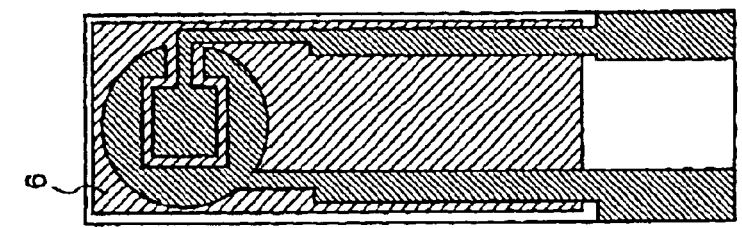
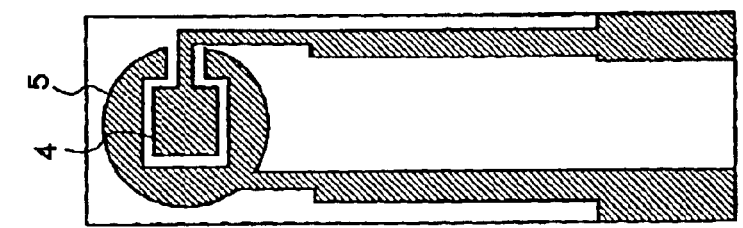
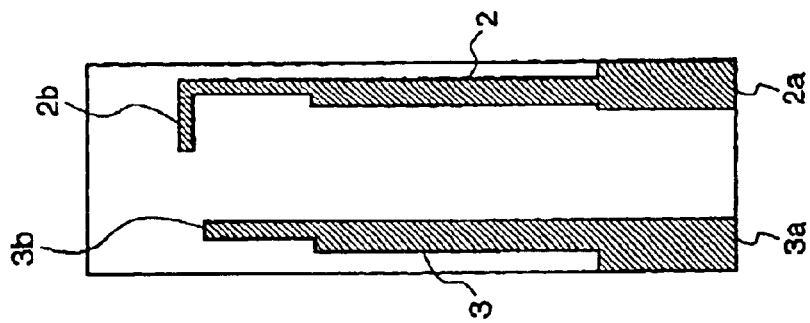
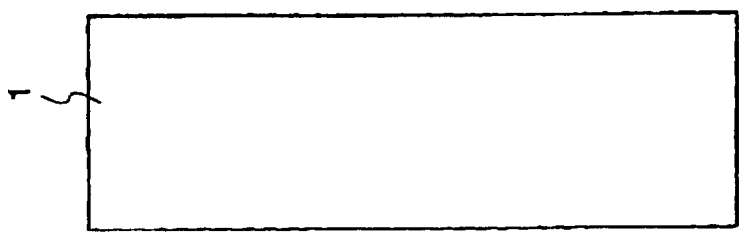

BIOSENSOR AND METHOD OF PRODUCING THE SAME

TECHNICAL FIELD

The present invention relates to a biosensor and a method for manufacturing the biosensor and, more particularly, to a biosensor which can speedily determine the quantity of a measurement target substance in a specimen liquid, and a method for manufacturing the biosensor.

BACKGROUND ART

There is a biosensor for measuring a specific measurement target substance in a specimen liquid, which measures an electric current value obtained by a reaction between glucose in blood and a reagent such as glucose oxidase, potassium ferricyanide, or the like supported in the sensor, thereby to obtain a blood sugar level.

FIG. 3 is an exploded diagram illustrating a process of manufacturing a conventional biosensor for measuring a blood sugar level.

A pair of conductive lead parts 2 and 3 stretching from a working electrode and a counter electrode to measuring terminals 2a and 3a is formed on a film insulating substrate 1 comprising polyethylene terephthalate or the like by screen printing or the like employing silver paste. End parts 2b and 3b of the conductive lead parts 2 and 3 are shaped to follow roughly a working electrode and a counter electrode to be formed afterwards. That is, the end part 2b of the conductive lead 2 is formed into a rectangle shape and the end part 3b of the conductive lead 3 is formed into a shape surrounding the rectangular shape. Then, a working electrode 4 and a counter electrode 5 of prescribed shapes are formed so as to overlap the respective end parts 2b and 3b, employing carbon paste.

Next, an insulating paste is overprinted on the insulating substrate 1 so as to expose the working electrode 4, the counter electrode 5, and the connection terminals 2a and 3a, thereby forming an insulating layer 6. A reaction layer 7, which includes carboxymethyl cellulose as a hydrophilic polymer, glucose oxidase as an enzyme, and potassium ferricyanide as an electron acceptor, is formed on the exposed working electrode 4 and counter electrode 5 so as to bridge these electrodes 4 and 5.

Thereafter, a cover, onto the reverse side of which a spacer 8 with a spindly specimen supply groove 10 having an opening part at its end formed is attached, is adhered so that an end part of the specimen supply groove 10 is located on the reaction layer 7, so as to cover the reaction layer 7 with the connection terminals 2a and 3a being left, as shown in FIG. 4. Numeral 11 denotes an air vent formed at the end part of the specimen supply groove 10.

When the sensor constructed as described above is connected to a measuring device and a blood sample to be measured is brought into contact with the opening of the specimen supply groove 10, a prescribed amount of sample is introduced into the reaction layer 7 through the specimen supply groove 10 by a capillary phenomenon, and a prescribed reaction between the glucose in the blood and the glucose oxidase as well as potassium ferricyanide supported in the sensor is developed. Then, an electric current value accompanying the reaction is read on the measuring device side through the connection terminals 2a and 3a, and the content of the glucose as the measurement target substance is measured from the electric current value.

However, in the case of the above-described conventional biosensor, the working electrode 4 and the counter electrode 5 are formed by overprinting carbon electrodes having almost the same shapes as the end parts 2b and 3b of the conductive lead parts which are formed of silver, by screen printing. Therefore, a pin hole or crack may be generated in the carbon electrode due to the printing state of carbon, the drying temperature, the attachment pressure of a top cover, or the like, whereby the conductive lead parts beneath the working electrode 4 and the counter electrode 5 are exposed to the surface to come into contact with the potassium ferricyanide which is the electron acceptor in the reaction layer 7, resulting in an increase in blank value and degradation of CV value (complete blood accuracy).

Further, regarding the working electrode, an increase in blank value and degradation of CV value occur due to an oxidation current of silver, resulting in degradation of sensor accuracy. Since the above-described problems have larger influences in a high-humidity environment, preservation in a dry condition is indispensable.

DISCLOSURE OF THE INVENTION

In order to solve the above-described problems, a biosensor according to the present invention is characterized by that the reaction layer which contacts the electrodes is not provided above at least one of the conductive lead parts, and even when a pin hole or a crack is generated in the both electrodes above the conductive lead parts, since the reaction layer is not provided in contact with the both electrodes in that portion, potassium ferricyanide and the conductive lead parts never contact. Further, an oxidation current of silver can be prevented at the working electrode, thereby providing a high-quality biosensor even in a high-humidity environment.

As described above, according to the invention, even when a pin hole or a crack is generated in the working electrode or the counter electrode, the electron acceptor, such as potassium ferricyanide, does not contact the conductive lead part, and further, an oxidation current of the lead part, which is made of a metal such as silver, can be completely prevented at the working electrode, whereby a high-quality biosensor which is excellent in preservation stability even in a high-humidity environment can be provided.

BRIEF DESCRIPTION OF DRAWINGS

FIG. 1 is an exploded diagram illustrating a process of manufacturing a sensor for measuring a blood sugar level according to an embodiment of the present invention.

BEST MODE TO EXECUTE THE INVENTION

Figure 2:
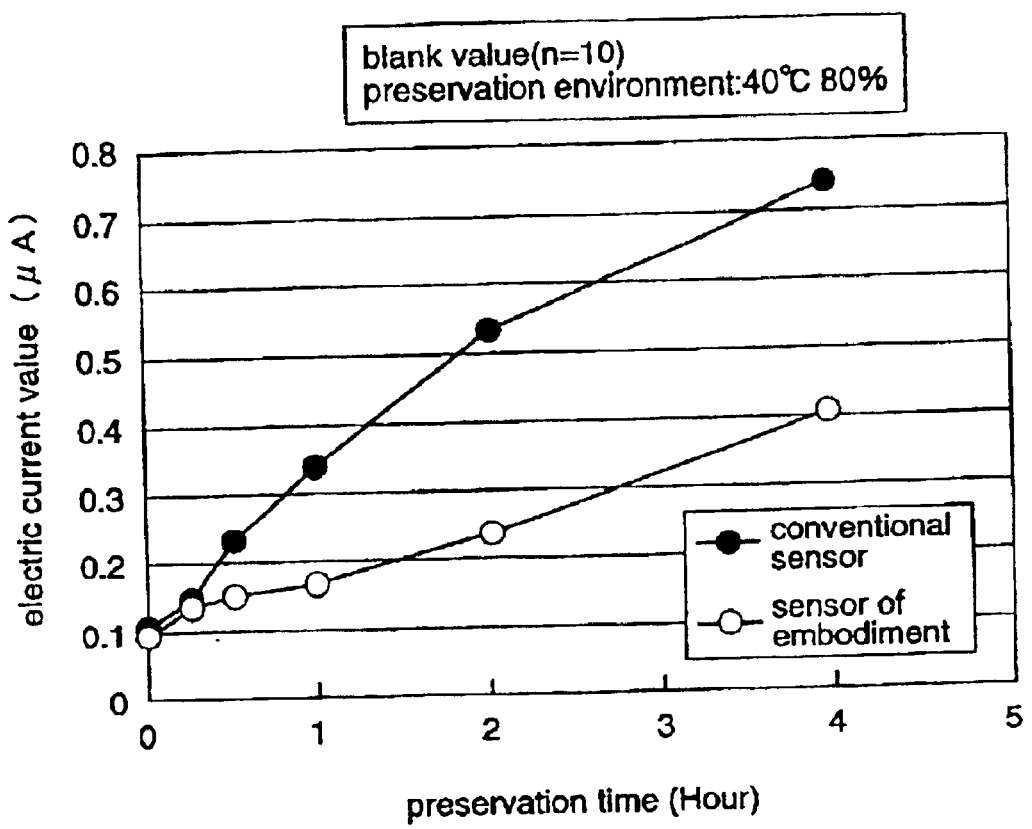
FIG. 2 is a diagram illustrating a comparison of CV values between the sensor for measuring a blood sugar level according to the embodiment of the invention and the conventional sensor for measuring a blood sugar level.
Figure 3E:
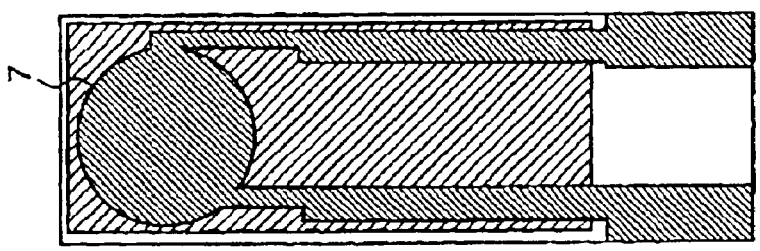
FIG. 3 is an exploded diagram illustrating a process of manufacturing the conventional sensor for measuring a blood sugar level.
Figure 3D:
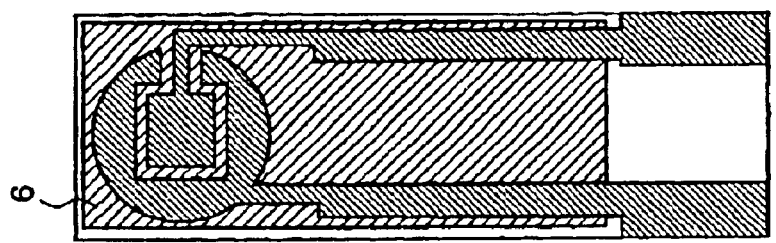
Figure 3C:
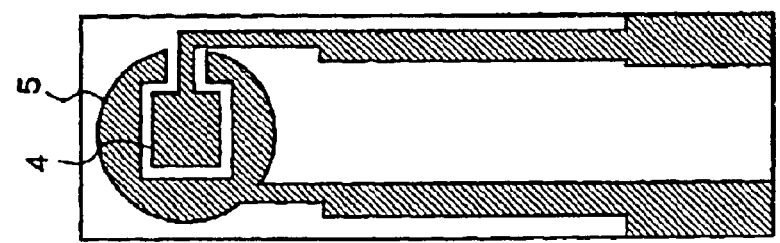
Figure 3B:
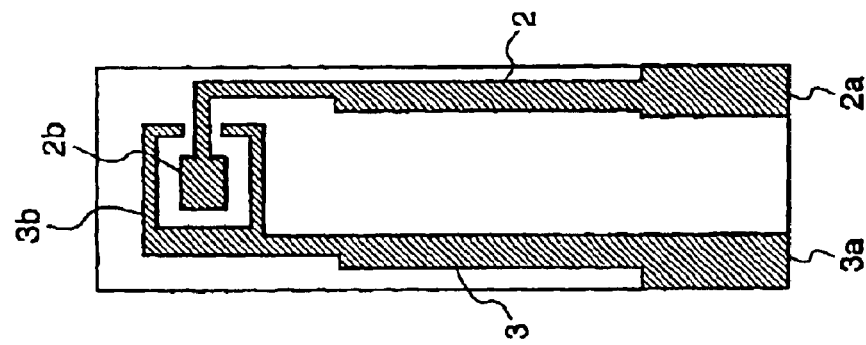
Figure 3A:
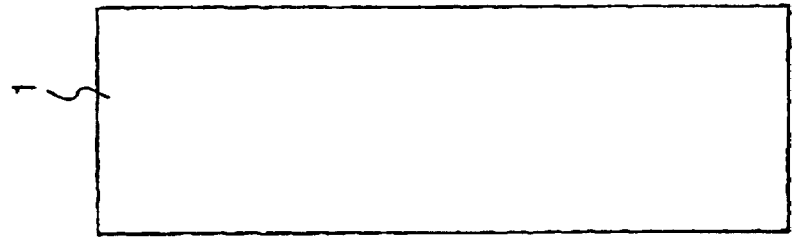

Hereinafter, a sensor for measuring a blood sugar level according to an embodiment of the present invention will be described with reference to FIG. 1. FIG. 1 is an exploded diagram illustrating a process of manufacturing the sensor for measuring a blood sugar level, and the same parts as those in the conventional constitution shown in FIG. 3 are denoted by the same reference numerals.

First of all, conductive lead parts 2 and 3 are formed of a metal material such as silver paste on a substrate 1 as in the conventional process. A difference from the conventional process is that end parts 2b and 3b of the conductive lead parts 2 and 3 are not shaped to follow a working electrode and a counter electrode as in the conventional process but are merely closed in straight lines. A working electrode 4 and a counter electrode 5, which are larger than prescribed shapes, are formed so as to partially overlap the end parts 2b and 3b of the lead parts, employing carbon paste which is mainly composed of carbon.

An insulating paste is overprinted on the substrate 1 of this state so as to expose the working electrode 4, the counter electrode 5, and the connection terminals 2a and 3a, thereby forming an insulating layer 6. At this time, portions of the working electrode 4 and the counter electrode 5 formed on the end parts 2b and 3b of the conductive lead parts are covered with the insulating layer 6.

A prescribed reagent reaction layer 7 which includes a hydrophilic polymer (carboxymethyl cellulose), an enzyme (glucose oxidase), and an electron acceptor (potassium ferricyanide) is formed on the electrodes 4 and 5 constructed as described above. At this time, even when the reaction layer 7 is extensively formed over the portions of the working electrode 4 and counter electrode 5 formed on the end parts 2b and 3b of the conductive lead parts, since these portions are covered with the insulating layer 6, the reaction layer 7 never comes in contact with the portions of the working electrode 4 and the counter electrode 5. That is, the reaction layer 7 is not substantially provided on the portions of the working electrode 4 and the counter electrode 5.

Thereafter, a cover 9 having a specimen supply groove 10 is adhered as in the conventional process, and also at this time, the specimen supply groove 10 is never positioned above the portions the end parts 2b and 3b of the conductive lead parts.

FIG. 2 illustrates a result obtained when purified water is measured (blank value) by the sensor of the above-described constitution, which is preserved in a hostile environment where the temperature is 40° and the humidity is 80%. An average at ten measurements is plotted, and it is shown that an increase in blank value can be suppressed even in a hostile environment of high temperature and humidity.

(Table 1) shows a comparison of sensor accuracy at twenty measurements with the blood glucose concentration of 42~600 mg/dl. The sensor accuracy is detected as follows. A reaction between a reagent and glucose in the blood is promoted for about twenty-five seconds after the blood is drawn into the capillary and, thereafter, a voltage of 0.5 V is applied between the connection terminal 2a of the working electrode and the connection terminal 3a of the counter electrode, and an electric current value is obtained five seconds later. The accuracy of variation in the electric current value is referred to as the sensor accuracy. The variation in measurement of the sensor according to this embodiment is significantly decreased and reduced as compared with that of the conventional sensor.

TABLE 1

| Glucose concentration | Conventional sensor | Sensor of embodiment |
|---|---|---|
| 42 mg/dl | 7.63% | 4.20% |
| 79 mg/dl | 3.47% | 2.75% |
| 245 mg/dl | 2.60% | 2.31% |
| 361 mg/dl | 2.45% | 2.20% |
| 497 mg/dl | 2.17% | 1.64% |
| 600 mg/dl | 3.81% | 1.40% |

Figure 4:
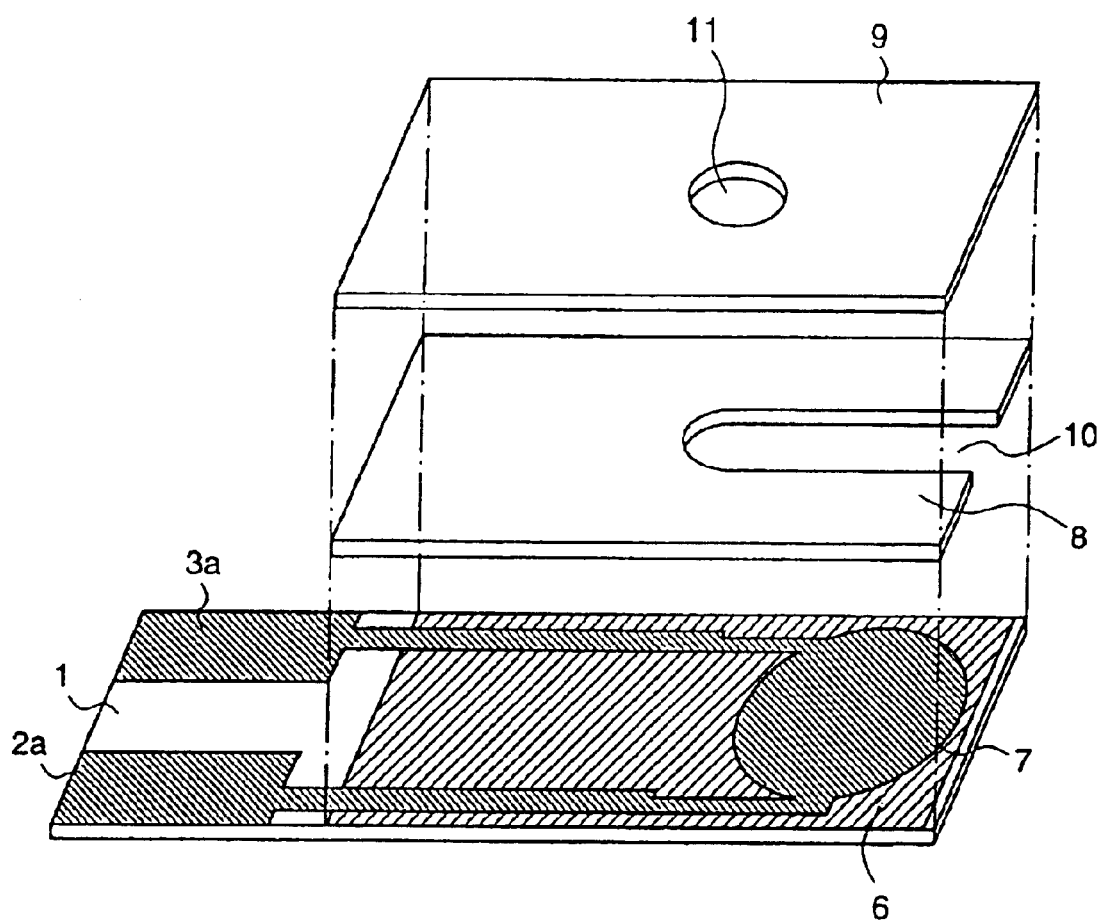
FIG. 4 is an exploded perspective view of the conventional sensor for measuring a blood sugar level.

As seen from FIG. 4 and the result of (Table 1), a biosensor which is excellent in preservation stability, is high in sensitivity, and has less variation can be realized by employing the sensor of this embodiment.

While a sensor for measuring a blood sugar level is exemplified in this embodiment, the same effects can be achieved even in a similarly constituted sensor for measuring cholesterol, lactic acid, or the like. Further, while it is most desirable that there is no reaction layer on the lead parts on both of the working electrode and the counter electrode, the same effects can be also achieved when there is no reaction layer on either one of them.

APPLICABILITY IN INDUSTRY

As described above, a biosensor according to the present invention can speedily determine the quantity of measurement target substance in a specimen liquid, thereby providing a biosensor which operates in high quality even in a high-humidity environment.

What is claimed is:

1. A biosensor comprising:
   a first conductive lead part comprising a metal and disposed on an insulating substrate;
   a second conductive lead part comprising a metal and disposed on the insulating substrate;
   a working electrode comprising carbon and disposed at a first end of said first conductive lead part and on the insulating substrate so that a portion of said working electrode overlaps said first conductive lead part;
   a counter electrode comprising carbon and disposed at a first end of said second conductive lead part and on the insulating substrate so that a portion of said counter electrode overlaps said second conductive lead part;
   a reaction layer including at least an enzyme and an electron acceptor,
   wherein said reaction layer is formed on said working electrode and said counter electrode so as to bridge said working electrode and said counter electrode,
   wherein said reaction layer reacts with a measurement target substance in a specimen liquid,
   wherein said reaction layer which contacts said working electrode and said counter electrode is not provided above said first and second conductive lead parts,
   wherein said reaction layer is covered with a cover having a specimen supply groove that has an opening at a first end thereof,
   wherein the specimen supply groove is operable to introduce the specimen liquid applied around the opening to said reaction layer, and
   wherein said first and second conductive lead parts are not located beneath the specimen supply groove.

2. A biosensor according to claim 1, wherein said reaction layer contacts only electrodes comprising carbon.

3. A biosensor manufacturing method comprising:

forming a first conductive lead part comprising a metal on an insulating substrate;

forming a second conductive lead part comprising a metal on the insulating substrate;

forming a working electrode comprising carbon at a first end of said first conductive lead part and on the insulating substrate so that a portion of said working electrode overlaps said first conductive lead part;

forming a counter electrode comprising carbon at a first end of said second conductive lead part and on the insulating substrate so that a portion of said counter electrode overlaps said second conductive lead part;

forming a reaction layer including at least an enzyme and an electron acceptor, wherein said reaction layer is formed on said working electrode and said counter electrode so as to bridge said working electrode and said counter electrode, wherein said reaction layer reacts with a measurement target substance in a specimen liquid, wherein said reaction layer which contacts said working electrode and said counter electrode is not provided above said first and second conductive lead parts, wherein said reaction layer is covered with a cover having a specimen supply groove that has an opening at a first end thereof, wherein the specimen supply groove is operable to introduce the specimen liquid applied around the opening to said reaction layer, and wherein said first and second conductive lead parts are not located beneath the specimen supply groove.

4. A biosensor manufacturing method according to claim 3, wherein the reaction layer contacts only electrodes comprising carbon.

* * * * *